United States Patent
Livne et al.

(10) Patent No.: US 8,491,548 B2
(45) Date of Patent: Jul. 23, 2013

(54) LIQUID STREAMING DEVICES AND METHOD OF USING SUCH DEVICES FOR TREATING WOUNDS

(75) Inventors: Sagi Livne, Givat Ada (IL); Amir Shiner, Givat Ada (IL); Refael Gil Koby, Kochav Yair (IL); Shlomo Namdar Kaufman, Tel-Aviv (IL)

(73) Assignee: EnzySurge Ltd., Rosh HaAyin (IL)

( * ) Notice: Subject to any disclaimer, the term of this patent is extended or adjusted under 35 U.S.C. 154(b) by 239 days.

(21) Appl. No.: 12/988,331

(22) PCT Filed: Apr. 21, 2009

(86) PCT No.: PCT/IL2009/000433
§ 371 (c)(1),
(2), (4) Date: Oct. 18, 2010

(87) PCT Pub. No.: WO2009/130696
PCT Pub. Date: Oct. 29, 2009

(65) Prior Publication Data
US 2011/0046577 A1      Feb. 24, 2011

Related U.S. Application Data

(63) Continuation of application No. 12/081,754, filed on Apr. 21, 2008, now Pat. No. 8,241,260.

(51) Int. Cl.
*A61M 35/00*       (2006.01)
(52) U.S. Cl.
USPC ............................ 604/289; 604/304; 604/305
(58) Field of Classification Search
USPC .......................................... 604/289, 290, 305
See application file for complete search history.

(56) References Cited

U.S. PATENT DOCUMENTS

| 551,973 A | 12/1895 | Knap |
| 3,874,387 A | 4/1975 | Barbieri |
| 4,250,882 A | 2/1981 | Adair |

(Continued)

FOREIGN PATENT DOCUMENTS

| WO | WO 98/38944 | 9/1998 |
| WO | WO 99/13793 | 3/1999 |

(Continued)

OTHER PUBLICATIONS

International Preliminary Report on Patentability Dated Nov. 4, 2010 From the International Bureau of WIPO Re. Application No. PCT/IL2009/000433.

(Continued)

*Primary Examiner* — Susan Su

(57) ABSTRACT

A liquid streaming device and method of using same for treating a wound includes a body having a lower surface for application to skin region around the wound to be treated and to conform to the contour of the skin region, and an upper surface facing outwardly when the body is applied to the skin region; a recess formed in the lower surface of the body and configured to enclose the wound when the body is applied to the skin region, and to define a chamber closed on one side by the skin region and the wound, and on the opposite side by the body; an inlet in the body on one side of the recess for introducing a treating liquid into an inlet side of the chamber; and an outlet in the body on another side of the recess for outletting the treating liquid from an outlet side of the chamber.

18 Claims, 16 Drawing Sheets

U.S. PATENT DOCUMENTS

| | | |
|---|---|---|
| 4,778,446 A | 10/1988 | Jensen |
| 4,969,880 A | 11/1990 | Zamierowski |
| 5,156,846 A | 10/1992 | Petersen et al. |
| 5,242,392 A | 9/1993 | Vaughn |
| 5,358,494 A | 10/1994 | Svedman |
| 5,441,482 A | 8/1995 | Clague et al. |
| 5,697,920 A | 12/1997 | Gibbons |
| 6,071,267 A | 6/2000 | Zamierowski |
| 6,095,992 A | 8/2000 | Augustine |
| 6,458,109 B1 | 10/2002 | Henley et al. |
| 6,520,982 B1 | 2/2003 | Boynton et al. |
| 6,685,681 B2 | 2/2004 | Lockwood et al. |
| 6,695,624 B1 | 2/2004 | Szu |
| 6,695,824 B2 | 2/2004 | Howard et al. |
| 6,752,794 B2 | 6/2004 | Lockwood et al. |
| 6,800,074 B2 | 10/2004 | Henley et al. |
| 6,824,533 B2 | 11/2004 | Risk, Jr. et al. |
| 6,942,649 B2 | 9/2005 | Ignon et al. |
| 6,960,981 B2 | 11/2005 | Blatz |
| 6,979,324 B2 | 12/2005 | Bybordi et al. |
| 7,077,832 B2 | 7/2006 | Fleischmann |
| 7,108,683 B2 | 9/2006 | Zamierowski |
| 7,144,390 B1 | 12/2006 | Hannigan et al. |
| 7,182,758 B2 | 2/2007 | McCraw |
| 7,195,624 B2 | 3/2007 | Lockwood et al. |
| 7,198,046 B1 | 4/2007 | Argenta et al. |
| 7,211,076 B2 | 5/2007 | Russell |
| 7,216,651 B2 | 5/2007 | Argenta et al. |
| 7,276,051 B1 | 10/2007 | Henley et al. |
| 7,316,672 B1 | 1/2008 | Hunt et al. |
| 7,381,859 B2 | 6/2008 | Hunt et al. |
| 7,422,576 B2 | 9/2008 | Boynton et al. |
| 2002/0068913 A1 | 6/2002 | Fleischmann |
| 2003/0093041 A1 | 5/2003 | Risk, Jr. et al. |
| 2004/0186421 A1 | 9/2004 | Freeman |
| 2005/0031860 A1 | 2/2005 | Okada et al. |
| 2005/0148913 A1 | 7/2005 | Weston |
| 2005/0256461 A1 | 11/2005 | DiFiore et al. |
| 2006/0015087 A1 | 1/2006 | Risk, Jr. et al. |
| 2006/0025727 A1 | 2/2006 | Boehringer et al. |
| 2006/0275526 A1 | 12/2006 | Benkovszki et al. |
| 2007/0005028 A1 | 1/2007 | Risk, Jr. et al. |
| 2007/0032762 A1 | 2/2007 | Vogel |
| 2007/0041960 A1 | 2/2007 | Freeman et al. |
| 2007/0167884 A1 | 7/2007 | Mangrum et al. |
| 2007/0219532 A1 | 9/2007 | Karpowicz et al. |
| 2007/0233022 A1 | 10/2007 | Henley et al. |
| 2007/0260226 A1 | 11/2007 | Jaeb et al. |
| 2009/0216204 A1 | 8/2009 | Bhavaraju et al. |
| 2009/0264838 A1 | 10/2009 | Livne et al. |
| 2009/0312723 A1 | 12/2009 | Blott et al. |

FOREIGN PATENT DOCUMENTS

| | | |
|---|---|---|
| WO | WO 03/101508 | 12/2003 |
| WO | WO 2004/037334 | 5/2004 |
| WO | WO 2006/052745 | 5/2006 |
| WO | WO 2006/114648 | 11/2006 |
| WO | WO 2006/133103 | 12/2006 |
| WO | WO 2007/031762 | 3/2007 |
| WO | WO 2008/008032 | 1/2008 |
| WO | WO 2008/013896 | 1/2008 |
| WO | WO 2008/043067 | 3/2008 |
| WO | WO 2008/040020 | 4/2008 |
| WO | WO 2008/041926 | 4/2008 |
| WO | WO 2009/130696 | 10/2009 |

OTHER PUBLICATIONS

Response Dated Nov. 23, 2011 to Official Action of Jun. 23, 2011 From the US Patent and Trademark Office Re. U.S. Appl. No. 12/081,754.

Notice of Allowance Dated Mar. 29, 2012 From the US Patent and Trademark Office Re. U.S. Appl. No. 12/081,754.

Response Dated Apr. 14, 2011 to Official Action of Feb. 16, 2011 From the US Patent and Trademark Office Re. U.S. Appl. No. 12/081,754.

Official Action Dated Jun. 23, 2011 From the US Patent and Trademark Office Re. U.S. Appl. No. 12/081,754.

International Search Report Dated Aug. 25, 2009 From the International Searching Authority Re.: Application No. PCT/IL2009/000433.

Written Opinion Dated Aug. 25, 2009 From the International Searching Authority Re.: Application No. PCT/IL2009/000433.

Official Action Dated Feb. 16, 2011 From the US Patent and Trademark Office Re. U.S. Appl. No. 12/081,754.

LIQUID STREAMING DEVICES AND METHOD OF USING SUCH DEVICES FOR TREATING WOUNDS

RELATED APPLICATIONS

This application is a National Phase of PCT Patent Application No. PCT/IL2009/000433 having International filing date of Apr. 21, 2009, which is a continuation of U.S. patent application Ser. No. 12/081,754 filed on Apr. 21, 2008, now U.S. Pat. No. 8,241,260. The contents of the above Applications are all incorporated herein by reference.

FIELD AND BACKGROUND OF THE INVENTION

The present invention relates to liquid streaming devices for treating wounds, and also to a method of using such devices for treating wounds.

Various types of wounds require various types of treatments, and a number of different devices have been developed for use in such treatments. These treatments include continuous streaming of a treating liquid that washes away secretions, exudates, debris and bacteria; drawing fluids from the wounds; and maintaining a moist wound bed. They also include continual autolytic and proteoloytic debridement by streaming saline or other debridement-augmenting agents, and protection of the wound from pathogens and contaminants in an aseptic therapeutic compartment. Exudate management may be effected by streaming of hyper-osmotic fluids to draw edematous fluids from the wound. In addition, low intensity vacuum conditions may be produced, which conditions are widely reported to remove edematous fluids and to facilitate formation of granulation tissue.

Examples of such liquid treating devices for treating wounds are described in U.S. Pat. Nos. 7,316,672, 7,276,051, 7,216,651, 7,211,076, 7,198,046, 7,144,390, 7,108,683, 6,960,981, 6,942,649, 6,695,824, 6,685,681, 6,071,267, 5,697,920, 5,441,482, 5,358,494, 5,242,392, 5,156,846, 5,218,973, 4,969,880 and 6,548,109. However, many of such known treatment devices do not stream a liquid across the wound, but merely draw fluids from the wound or maintain a moist wound bed, and therefore are not particularly effective to wash away secretions, exudates, debris, bacteria, etc. Others of such devices, which are particularly useful for streaming liquids across the wound, are not convenient to apply and/or to wear by the patient.

OBJECT AND BRIEF SUMMARY OF THE PRESENT INVENTION

One object of the present invention is to provide a liquid streaming device for treating wounds in a manner which can be advantageously used in one or more of the above treatments and also for effecting a plurality of such treatments at the same time. Another object of the invention is to provide a method of treating a wound using such liquid streaming devices.

According to one broad aspect of the present invention, there is provided a liquid streaming device for treating a wound, comprising: a body having a lower surface for application to skin region around the wound to be treated and to conform to the contour of the skin region, and an upper surface facing outwardly when the body is applied to the skin region; a recess formed in the lower surface of the body and configured to enclose the wound when the body is applied to the skin region, and to define a chamber closed on one side by the skin region and the wound, and on the opposite side by the body; an inlet in the body on one side of the recess for introducing a treating liquid into an inlet side of the chamber; and an outlet in the body on another side of the recess for outletting the treating liquid from an outlet side of the chamber.

According to further features in the described preferred embodiments, the device further comprises an elongated distribution channel in the body for conducting the treating liquid from the inlet to the inlet side of the chamber. The elongated distribution channel extends around the inlet side of the chamber defined by the recess, and communicates with a plurality of short, spaced, distribution channels for distributing the treating liquid into the inlet side of the chamber defined by the recess. The plurality of short distribution channels have outlets oriented to direct the treating liquid substantially downwardly into the wound.

According to still further features in the described preferred embodiments, the outer surface of the body overlying the recess is of dome shape to prevent its collapse and contact with the skin by a negative pressure therein. At least a portion of the body overlying the recess is transparent to permit visual observation of the interior of the chamber.

In the described embodiments, the body is a thin flexible manifold of an elastomeric material and includes an enlarged area at its center region for accommodating the chamber, and relatively small areas at opposite end regions for accommodating the inlet and outlet channels. Also, the body further includes an adhesive on its lower surface for adhering the body to a skin region around the wound and for sealing the chamber.

In some described preferred embodiments, the body is a thin flexible body including an upper layer and a lower layer formed with an opening defining the recess and the chamber; the inlet and outlet channels are formed in the facing surfaces of the two layers.

In another described embodiment, the body is an integral body of elastomeric material formed with the recess defining the chamber, and further formed with the inlet and outlet.

According to another aspect of the invention, there is provided a method of treating a wound by a streaming device as described above wherein the streaming device is attached to the skin region around the wound to be treated to define the chamber over the wound. The inlet of the streaming device is connected to a source of treating liquid at an elevation above the wound to initially produce a positive pressure in the treating liquid for filling the chamber; and the outlet of the streaming device is connected to a collection receptacle at an elevation below the wound to produce, when a restricted liquid flow is produced in the chamber, a negative pressure in the chamber.

As will be described more particularly below, such a liquid streaming device permits therapeutic or other liquids to be administered to the wound bed to perform one or more of the above-described treatments in a convenient and effective manner.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
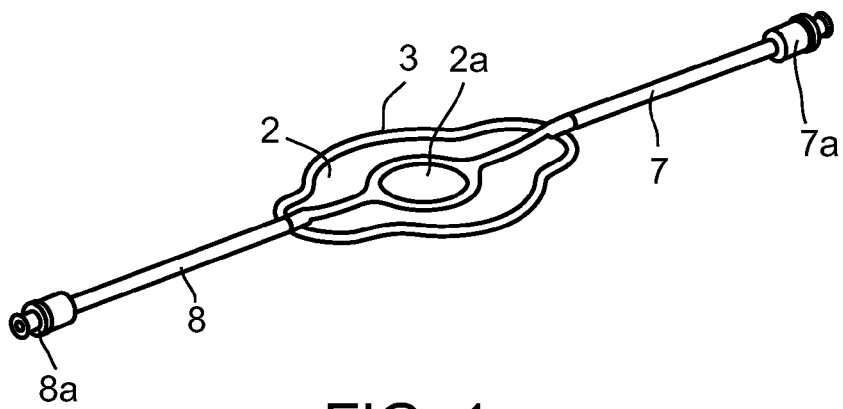
FIG. 1 illustrates one form of streaming device constructed in accordance with the present invention for treating wounds.
Figure 2:
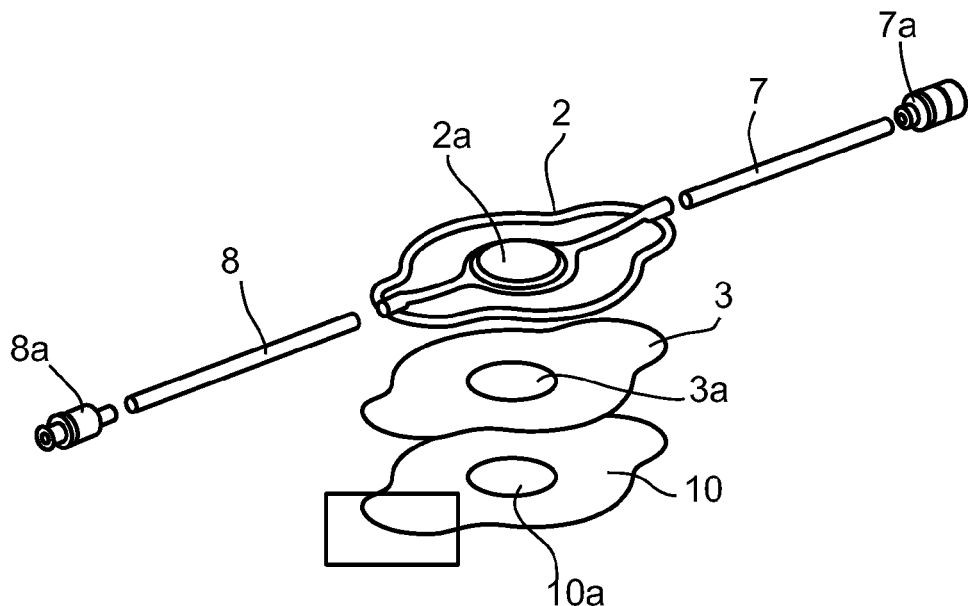
FIG. 2 is an exploded view of the main part of the device of FIG. 1.

FIG. 1 is a three-dimensional view, and FIG. 2 is an exploded view, illustrating the main parts of one form of liquid streaming device constructed in accordance with the present invention. Thus, as shown in FIG. 2, such a liquid streaming device includes an upper layer 2 of a material bonded to a lower layer 3 of material. Preferably, both layers 2 and 3 are of an elastomeric material, such as a silicone. TPE (thermoplastic elastomer), etc. Before the two layers are bonded together, the upper layer 2 is formed, in the central area of its under surface, with a partially-circular recess in the form of a loop 4 (FIG. 4) closed at its opposite ends to define an interrupted region 4a in the loop; a linear recess 5 extending from one end of layer 2 to the central portion 2a of layer 2 enclosed by the partially-circular loop 4; and a second linear recess 6 extending from the interrupted portion 4a of loop 4 to the opposite end of the layer.

The lower layer 3 is formed, before it is bonded to the upper layer 2, with a central opening 3a (FIG. 2) of a diameter to cover the partially-circular loop 4 of the upper layer 2, but to leave uncovered the central portion 2a of layer 2 enclosed by the partially-circular loop 4, uncovered.

After the two layers 2 and 3 have been bonded together, a flexible inlet tube 7 is introduced into a linear recess channel 5 such that one end of tube 7 communicates with the mid-portion of partially-circular loop 4, while the opposite end includes a funnel connector 7a. A flexible outlet tube 8 is introduced into a linear recess or channel 6 so that one end leads to the interrupted portion 4a of the partially-circular loop, whereas the opposite end extends outwardly and includes a funnel connector 8a.

After the two layers 2 and 3 have been bonded together and the flexible tubes 7 and 8 located within linear recesses 5 and 6, respectively, a pressure-sensitive adhesive assembly 10, formed with a central opening 10a for alignment with opening 3a in the lower part 3, is applied to the under surface of the lower layer 3. Adhesive assembly 10 enables the illustrated liquid streaming device to be conveniently applied to the patient's skin around the wound, as will be described more particularly below.

FIGS. 1 and 2-5 illustrate the construction of the liquid streaming device after the foregoing parts have been made and assembled together as described above. Thus, layers 2 and 3 define a body serving as a manifold, having a lower surface for application to the skin region (S, FIG. 10) around the wound (W, FIG. 10) to be treated with a liquid, and an upper surface, namely the outer surface of the upper layer 2, to face outwardly when the body is applied to the mentioned skin region. Opening 3a formed in the lower layer 3, and opening 10a in the adhesive assembly 10, define a circular recess which encloses the wound when the thin flexible body, defined by the two bonded layers 2, 3, is applied by the adhesive assembly to the skin region around the wound.

The two layers 2, 3 thus define a liquid treatment chamber 9 closed on one side by the skin region S (FIG. 10) and the wound W, and on the opposite side by the central portion 2a of the upper layer 2 overlying opening 3a. An inlet is defined by linear recess 5 and inlet tube 7 for introducing a treating liquid into the inlet side of chamber 9. An elongated distribution channel is defined by the partially-circular loop 4 for conducting the treating liquid from the inlet to the inlet side of chamber 9; and an outlet is defined by linear recess 6 and outlet tube 8 for outletting the treating liquid from the loop-interrupted side 4a defining the outlet end of chamber 9.

Figure 3A:
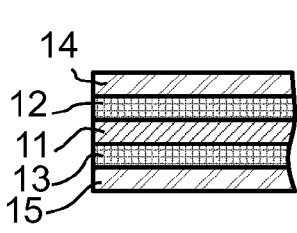
FIGS. 3a-3c are fragmentary sectional views illustrating two types of adhesive assemblies that could be used in the liquid streaming device of FIG. 2.
Figure 3B:
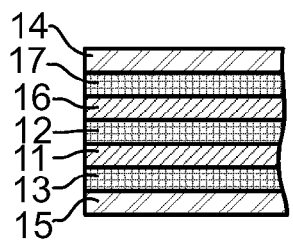
Figure 3C:
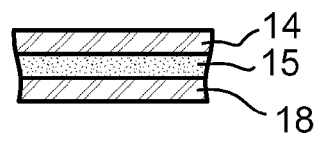

As indicated earlier, the two layers 2 and 3 are preferably made of an elastomeric material, such as silicone or TPE. This enables the body to be conveniently applied to the patient's skin, and to permit substantially unrestricted movement of the respective part of the patient's body. Silicone is difficult to adhere to a patient's skin, which is a reason for including the adhesive assembly 10. FIGS. 3a, 3b and 3c illustrate three types of adhesive assemblies 10 which may be used for this purpose.

FIG. 3a illustrates a five-layer construction, and FIG. 3b illustrates a seven-layer construction, which may be used particularly where the two layers 2, 3, of the body are made of a silicone elastomer or TPE.

The five-layer construction illustrated in FIG. 3a includes a plastic film carrier 11, preferably of an elastomeric material such as polyurethane or TPE (thermoplastic elastomer) material. However, carrier 11 may also be another material, such as polyethylene, which is a thin, flexible, non-elastomeric material, a nonwoven material or a foamed material. One side of carrier film 11 carries a layer of adhesive 12 having good adherent properties with respect to silicone or TPE; such an adhesive may be, for example, an acrylic/silicone adhesive. The opposite side of carrier film 11 carries another layer 13 of adhesive having good adherent properties to the skin, such as a hydrocolloid adhesive. Both adhesive layers 12 and 13 are each covered by a release liner 14 and 15, respectively.

The seven-layer construction, generally designed 10' in FIG. 3b, includes the same five layers as described above in assembly 10 of FIG. 3a, which layers are correspondingly numbered as in FIG. 3a. In addition, adhesive assembly 10' in FIG. 3b includes two additional layers, namely another plastic film carrier 16 having a lower face adhered to adhesive layer 12, and an upper face carrying another adhesive layer 17 covered by the release liner 14. In the construction illustrated in FIG. 3b, the additional plastic film carrier 16 may be one of the same materials as plastic carrier 11 in FIG. 3a; alternatively, it may also be a nylon film, a nonwoven fabric layer, or a foamed layer, having good adherent properties with respect to the acrylic/silicone adhesive of layer 12 and good strength properties to increase the strength of the adhesive assembly.

The three-layer adhesive assembly illustrated in FIG. 3c is particularly useful where the adhesive used has good adherent properties both to the lower layer 3 of the streaming device and the skin of the patient. In such case, the adhesive assembly illustrated in FIG. 3c, and therein designated 10'', includes an upper release liner 14 and a lower release liner 15 with an adhesive layer 18 between the two liners. Thus, when the adhesive assembly is to be applied to the streaming device, the upper liner 14 is peeled away, and the adhesive layer 18 is applied to the under surface of the streaming device. When the streaming device is to be applied to a patient, the lower liner 15 is peeled away, to enable the streaming device to be adhesively applied to the patient's skin.

Figure 10:
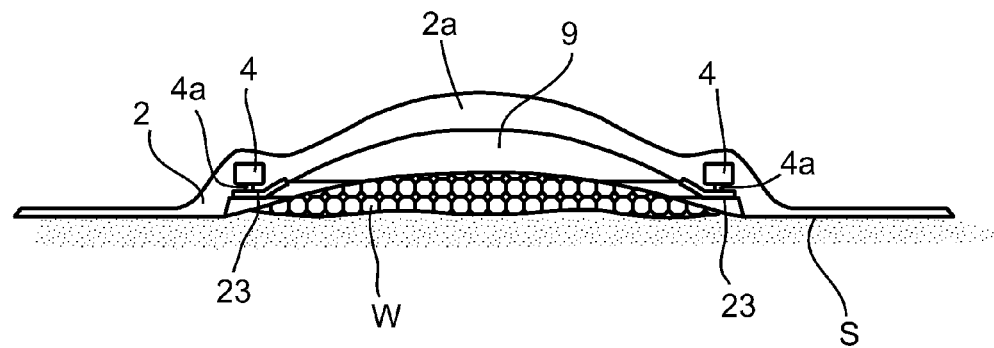
FIG. 10 schematically illustrates a modification wherein the elongated distribution channel is formed with a plurality of short distribution channels having downwardly-extending outlets spaced from the wound to prevent their blockage when the treating chamber exposed to the wound is under suction.

Adhesive assembly 10 of FIG. 3a, 10' of FIG. 3b, and 10'' of FIG. 3c, is of the same configuration as the lower layer 3 of the body produced the two layers 2, 3 together. As indicated above, each adhesive assembly is formed with a central opening 10a aligned with central opening 3a of layer 2.

Adhesive assembly 10 of FIG. 3a, 10' of FIG. 3b, or 10'' of FIG. 3c may be conveniently applied to the under surface of the lower layer 3, by first peeling away the upper release liner 14 and then applying the adhesive layer (e.g. 12 of FIG. 3a, 17 of FIG. 3b or 18 of FIG. 3c) to the under surface of layer 3. Whenever the device is to be applied to the skin of the patient to treat a wound therein, the lower release liner 15 is peeled away to thereby expose the hydrocolloid adhesive layer 13 for contact with the subject's skin. As indicated above, when the device is so applied, opening 10a in adhesive assembly 10, and opening 3a in the lower layer 3, define chamber 9 enclosing the wound and closed on one side by the central portion 2a of the upper layer 2, and on the opposite side by the skin S (FIG. 10) and wound W.

As shown particularly in FIG. 10, the central region 2a of the upper layer 2 is preferably outwardly bulged to a dome-shape to structurally strengthen the chamber against collapse and to prevent contact with the wound in the presence of a high negative pressure within the treatment chamber 9. Preferably, this region of layer 2, or the complete layer 2, is of a transparent material so as to enable visual observation of the wound within the chamber.

Figure 4:
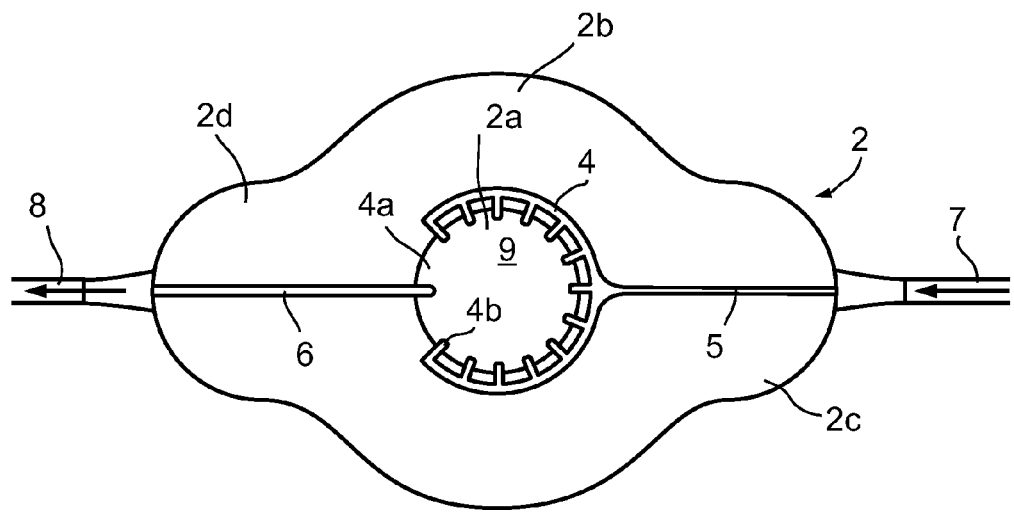
FIG. 4 more particularly illustrates the liquid channels in the liquid streaming device of FIGS. 1 and 2.
Figure 5:
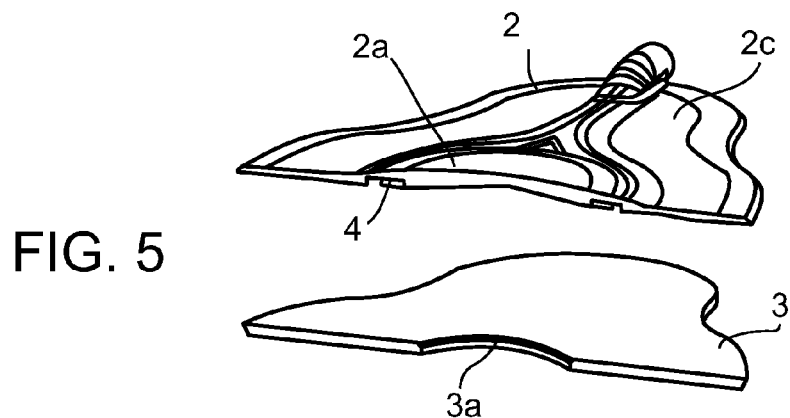
FIG. 5 is an exploded fragmentary top view of FIG. 2.
Figure 6:
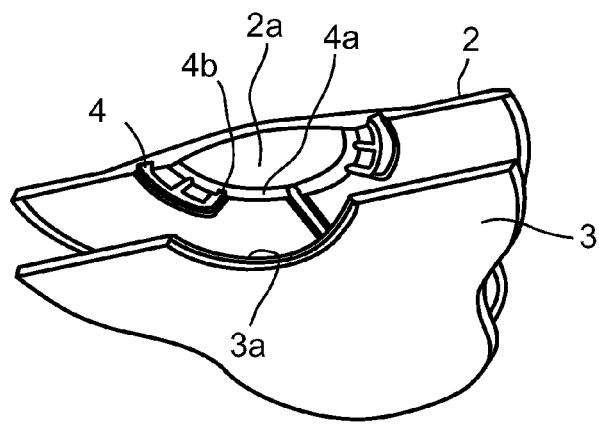
FIG. 6 is an exploded fragmentary bottom view of FIG. 2.
Figure 7:
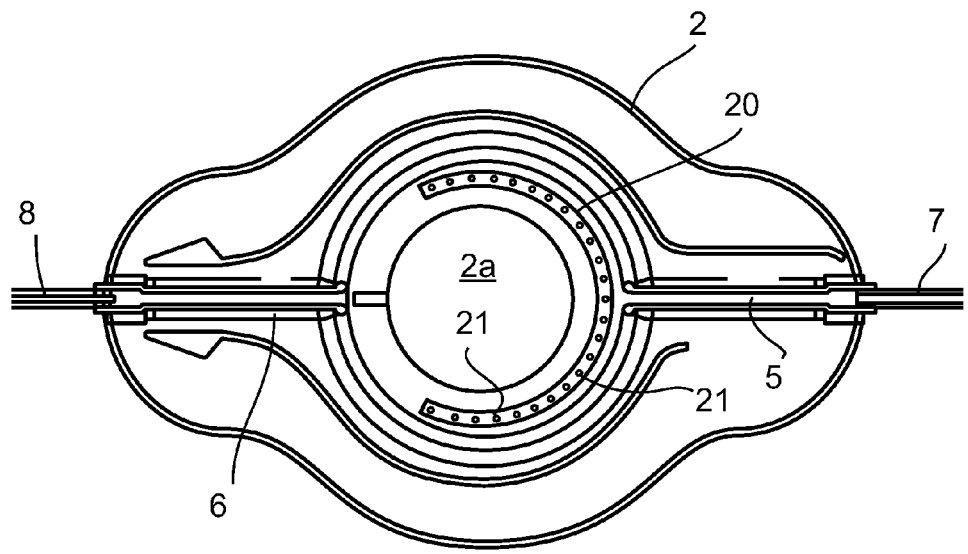
FIG. 7 illustrates a variation in the upper part of the device of FIG. 4, wherein the distribution openings are downwardly-oriented orifices.

As shown particularly in FIGS. 4-6, the elongated distribution channel defined by the partially-circular loop 4 includes a plurality of downwardly-extending short channels 4b leading into chamber 9 so as to uniformly distribute the treating liquid around the circumference of the chamber. The short distribution channels 4b are preferably downwardly oriented so as to better conduct the treating liquid into the depth of the wound within chamber 9. This may be done by forming the semi-circular loop constituting the elongated distribution channel 4 with downwardly-extending extensions spaced along the length of the loop as shown in FIG. 4, or with orifices in the lower surface of the loop, as shown in FIG. 7, or in the embodiment of FIGS. 8 and 9 described below.

The upper layer 2 is of an enlarged area in its central region 2b (FIG. 4) for accommodating the liquid treatment chamber 9 defined by the central domed region 2a, and also the looped distribution channel 4 communicating with the inlet side of that chamber. The two end regions 2c, 2d, of the upper layer 2, are of reduced area to accommodate the inlet and outlet channels 5, 6. It will also be seen that the lower layer 3 is of similar configuration as the upper layer 2.

The above-described streaming device of FIGS. 1-7 may be used to treat a wound in the following manner:

First, the upper release liner 14 is removed to expose the adhesive 12 (FIG. 3a) or 17 (FIG. 3b) for application to the under surface of the lower layer 3. Release liner 15 is then removed and the streaming device is applied to the skin region S (FIG. 10) around the wound W (FIG. 10) to define the treatment chamber 9, which, as pointed out above, is closed at one side by the central region 2a of the upper layer 2, and on the opposite side, by the wound W and the skin region S around the wound. The inlet tube 7 is then connected to a source of treating liquid at an elevation above the wound, and the outlet tube 8 is connected to a collection receptacle at an elevation below the wound. Thus, a gravity-flow of the treating liquid to the treatment chamber 9 is initially produced by the positive pressure to fill chamber 9 with the liquid. A negative pressure is produced in the chamber by its connection to the low-elevation collection receptacle. This negative pressure applied to the wound within the chamber varies with the rate of flow to the collection receptacle.

Administration of therapeutic or other liquids to the wound is thus made possible through the device's streaming mechanism. The continuous streaming of the treating liquid effectively washes away secretions, exudates, debris and bacteria, and also maintains a moist wound bed. Such continuous streaming can be used for producing a continual autolytic or proteolytic debridement by streaming saline or other debridement augmenting agents. The liquid streaming device thus may be used to enhance a wound healing process, and also to protect the wound from pathogens and contaminants in an aseptic therapeutic compartment, namely the treatment chamber 9. The streaming device can also be used to manage exudates by streaming hyper-osmotic fluids to draw edematous fluids from the wounds or hypo-osmotic fluids to drive therapeutic agents into the wound. The low-intensity vacuum produced within chamber 9 tends to remove edematous fluids and facilitates formation of granulation tissue.

Flow-restricting devices, commonly used in standard intravenous sets, may be used to control the flow rate. The flow-restricting device may be set to produce a flow ranging up to 3000 ml/hour, i.e., up to 50 ml/minute. The height difference between the source of the treating liquid, usually a fluid bag, and the wound ensures gravity flow to chamber 9, while the height difference between the wound and collection bag ensures a low intensity, therapeutic vacuum in chamber 9.

A uniform flow of the treating liquid into the treatment chamber 9 may be produced by suitably designing the distribution, the length and the diameters of the short flow distribution channels or orifices 4b located around the looped elongated distribution channel 4, to inlet the treating liquid into the treatment chamber uniformly around its periphery. In addition, the downwardly-oriented ends or orifices of the short distribution channels 4b, produce a flow perpendicularly to the wound bed W, thereby creating a downward velocity component to the treating liquid introduced into the treatment chamber 9. This flow mechanism prevents the formation of a stagnant flow region at the wound bed that could impede the cleansing and treatment functions of the treating liquid.

The connector 7a, at the outer ends of the inlet tube 7, preferably includes a luer-activated check valve. Such valves are normally closed, but are automatically opened when a luer male connector is inserted. This allows the patient to disconnect the streaming device from the infusion set without removing the streaming device. When disconnected, the streaming device remains airtight and attached to the patient's skin. The wound is thus protected from contamination and injury, while a moist and therapeutic environment is maintained. The check valve in connector 7a also allows multiple treatment sessions without risking infection in the wound.

Since the illustrated streaming device is made of a soft and flexible elastomeric material, it may be bent to assume the contour of the skin area to which it is applied. In addition, the illustrated flat, thin streaming device has a low profile shape, one that allows it to behave as a two-dimensional structure. In this way, it exhibits low resistance to deformation and may be wrapped easily around the body part to which it is applied. The streaming device lies flat against the skin, stretching with the skin as the patient moves about. Its low profile allows patient mobility since it does not have extraneous parts that might interfere with patient movement.

Flow optimization of the treating liquid through the streaming device may be effected by taking into consideration the following factors:

(a) The vacuum inside the treatment chamber 9 covering the wound mainly depends on the vertical distance between the outlet bag (collection) and the patient. This means that the larger the vertical distance between the patient and the collection bag, the larger is the vacuum level created around the wound. The following table shows the pressure gradient as function of the distance in a no flow condition:

| Distance [cm] | Millibar | Millimeters of mercury |
| --- | --- | --- |
| 0 | 0 | 0 |
| 10 | −10 | −7.5 |
| 2- | −20 | −15 |
| 3-0 | −30 | −22.5 |
| 40 | −40 | −30 |
| 50 | −50 | −37.5 |
| 60 | −60 | −45 |
| 70 | −70 | −52.5 |
| 80 | −80 | −60 |
| 90 | −90 | −67.5 |
| 100 | −100 | −75 |

(b) The vacuum also depends on the flow entering chamber 9. The higher the flow, the lower is the vacuum generated in the chamber. For example for a flow of 0 [cc/min], when the treating liquid fills the entire system, the vacuum in case of positioning the collection bag 50 cm below the patient would result in −37.5 mm of mercury. On the other hand for the same setup, if passing a flow of a few tens of cc/min, the vacuum will sharply decrease to −32 mm of mercury.

(c) An increase in flow is possible by either increasing the flow area to the flushing chamber (controlled via an orifice) or by just increasing inlet diameter or pressure. The inlet pressure can be increased by elevating the inlet bag.

It will be thus be seen the optimal vacuum and flow are created by the combination of maximum distance between the patient and the collection bag, while minimum flow is achieved by lowering the inlet bag, reducing the orifice of the inlet and outlet tubes, or creating the equivalent flow path by using narrow tubes.

It may also be desirable to modulate the intensity of the negative pressure in the chamber. This can be done by altering the height of the bag, or by controlling the flow rate of the liquid into the collection bag. This may also be accomplished by providing a controllable pressure source and/or vacuum source connected to the inlet and outlet, respectively, of the treatment chamber such as to control, or to modulate, the pressure within the treatment chamber.

Figures 8, 9:
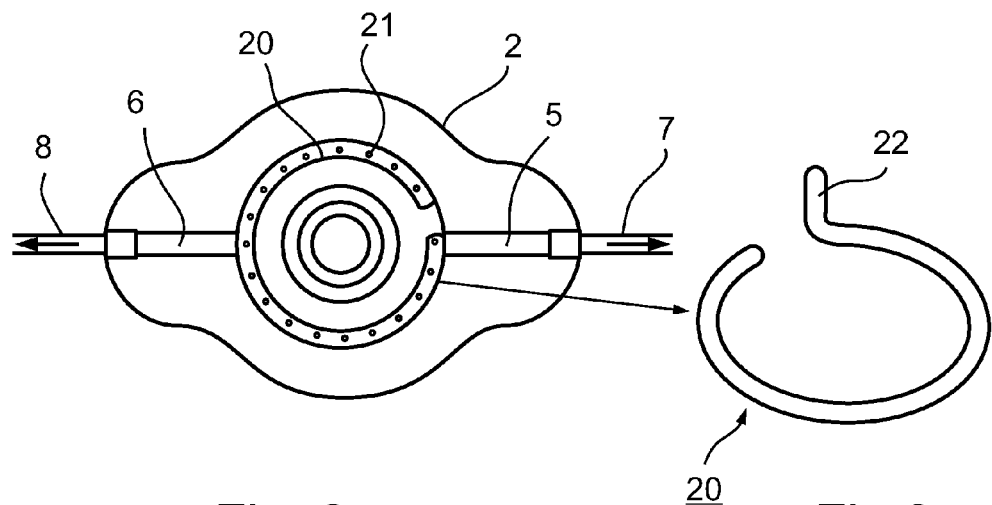
FIGS. 8 and 9 illustrate a modification of the streaming device wherein the elongated distribution channel is a flexible tube perforated with downwardly-oriented orifices.

FIGS. 8 and 9 illustrate an embodiment of the invention somewhat similar to those of FIGS. 1-7, and therefore corresponding parts are identified by the same reference numerals for purposes of clarity. The main difference in the embodiment of FIGS. 8 and 9 is in the construction of the distribution channel, therein designated 14, for distributing the treating liquid into the inlet side of treatment chamber 9.

Thus, as shown in FIG. 8, the distribution channel includes a flexible tube 20, which is interposed between the two layers 2 and 3 before they are bonded together. For this purpose, flexible tube 20 is snap-fitted into a recess corresponding to the partially-circular recess defining loop 4 (FIG. 4) or 4' (FIG. 7) formed in the under face of the upper layer 2. Flexible tube 20 is provided with a plurality of downwardly-oriented orifices 21 varying in size along the length of the tube to distribute the treating liquid uniformly into the inlet end of chamber 9 around its periphery.

Flexible tube 20 is preferably further provided with a stiff but bendable end portion 22 (FIG. 9) at one or both of its ends in order to deliver the treating liquid directly into a deep wound bed, if so desired.

Figures 11, 12:
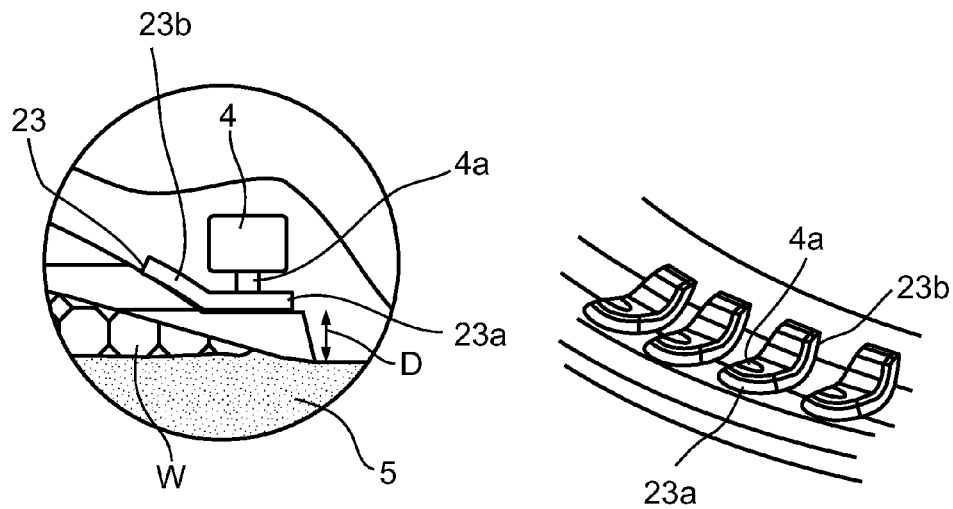
FIG. 11 is a fragmentary enlarged view of a portion of FIG. 10.
FIG. 12 more particularly illustrates the spacing ribs in FIGS. 10 and 11 for spacing the outlet ends of the distribution channels from the wound to prevent blockage when suction is applied to the liquid treating the chamber.

FIGS. 10-12 illustrate a feature which may be included in any of the embodiments described herein, wherein the outlets of the orifices or short distribution channels 4a of the loop elongated channel 4 are spaced away from the wound W to prevent blockage of the outlets when the treatment chamber 9 is under a negative pressure.

The feature of FIGS. 10-12 is illustrated with respect to the embodiment of FIGS. 1-7, wherein the elongated distribution loop 4 is defined by a partially-circular channel formed in the under surface of the upper layer 2, and includes a plurality of downwardly-oriented short ducts 4a leading into the inlet side of chamber 9. As shown in FIGS. 10-12, a plurality of spacer elements 23 are secured to the underside of loop 4. Each of the spacer elements 23 includes one leg 23a to which the downwardly-oriented or short ducts 4a pass, and a second leg 23b for spacing the outlets of the short ducts above the skin S and wound W a short distance, shown at D in FIG. 11, above the skin and the wound such as to prevent blockage of the outer ends of the short distribution ducts 22 when chamber 9 is subjected to a negative pressure.

As indicated above, although the feature of FIGS. 10-12 is illustrated with respect to the embodiment of FIGS. 1-7, the same feature can be included in the previously-described, or later-to-be-described, embodiments.

Figure 13:
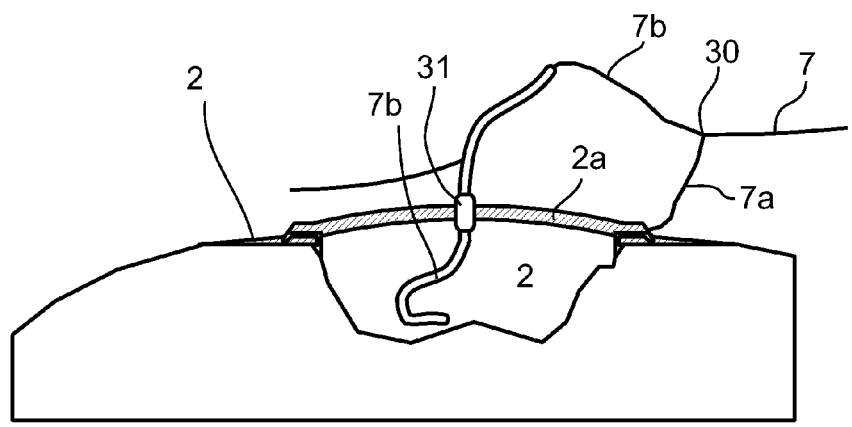
FIG. 13 illustrates a modification, wherein the streaming device includes another inlet channel receiving an inlet conduit passing through the center of the upper part to treat deep wounds.

FIG. 13 illustrates a further optional feature wherein inlet tube 7 includes a Y-fitting 30 to supply the treating liquid through one inlet tube 7a connected to the inlet side of the treatment chamber 9, and through a second tube 7b passing through a hole 31 in the central dome part 2a of the upper layer 2 in order to direct a portion of the liquid more deeply into the wound W. If this is not required, tube 7b and hole 31 may be sealed with plugs (not shown).

It will be appreciated that the above feature illustrated in FIG. 13 could also be used in any of the previously-described, or later-to-be-described, embodiments of the invention.

Figure 14:
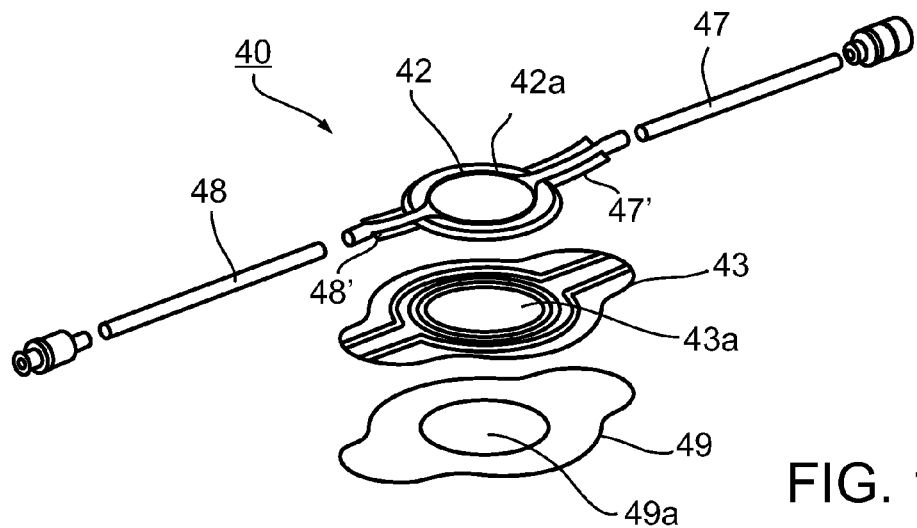
FIG. 14 is an exploded view illustrating another embodiment of the invention, wherein the upper part is of smaller area than the lower part.
Figure 15:
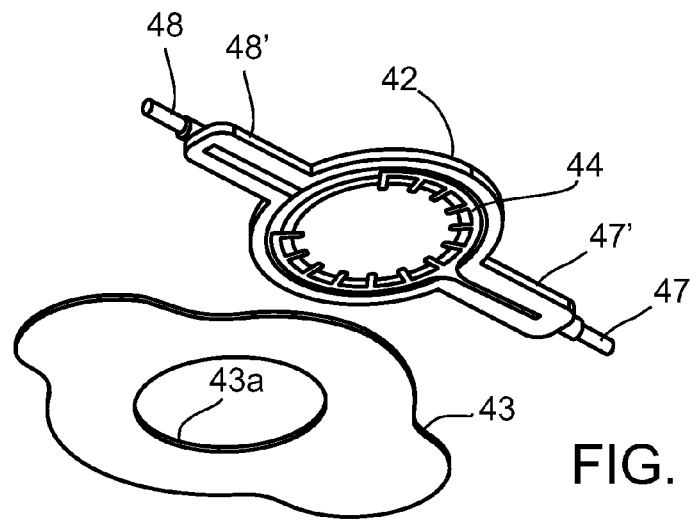
FIGS. 15 and 16 are exploded views from opposite sides of the streaming device of FIG. 14.
Figure 16:
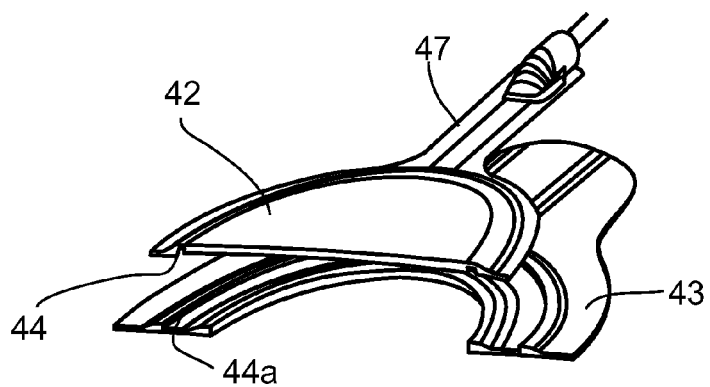

In the foregoing constructions, the upper layer 2 and the bottom layer 3 are of the same configuration and size, including an enlarged central area 2b (FIG. 4) for accommodating the treatment chamber 9 (FIG. 10), and two reduced-area end sections 2c, 2d for accommodating the inlet and outlet conduits. FIGS. 14-16 illustrate a streaming device wherein the upper layer, generally designated 42, is of smaller area than the lower layer 43. In this case, the upper layer 42 is formed with a central region 42a (which may be dome-shaped, flat-shaped, etc.), the looped distribution channel 44, and the inlet and outlet tubes 47, 48; received in channels 47', 48' integrally formed with channel 44', whereas the lower layer 43a is formed with an annular seat 43a for part 42 defining the central opening for the treatment chamber. In all other respects, the streaming device 40 illustrated in FIGS. 14-16 is constructed substantially the same as described above, including the adhesive assembly 49 which may be as described above with respect to adhesive assembly 10 (FIG. 3a) or 10' (FIG. 3b).

The construction illustrated in FIGS. 14-16 provides several advantages: First, it increases the flexibility of the overall liquid streaming device because of the reduced thickness both at its middle portion and at its end portions; secondly, it substantially reduces material costs since less elastomeric material is used for the upper layer.

Figure 17:
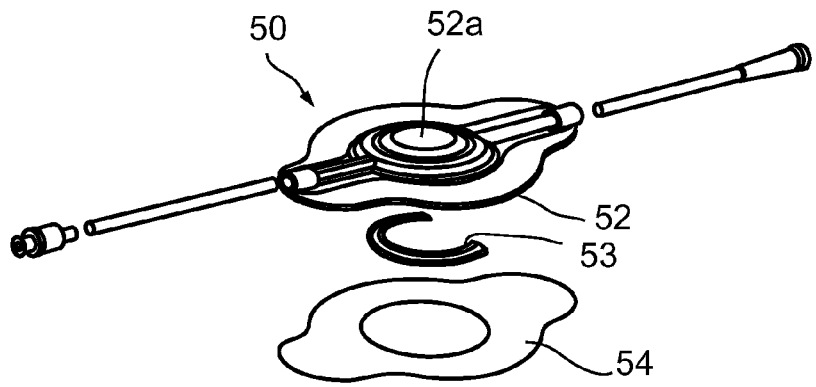
FIG. 17 is an exploded view illustrating a further streaming device constructed in accordance with the present invention wherein the lower part of the device is of smaller area than the upper part.
Figure 18:
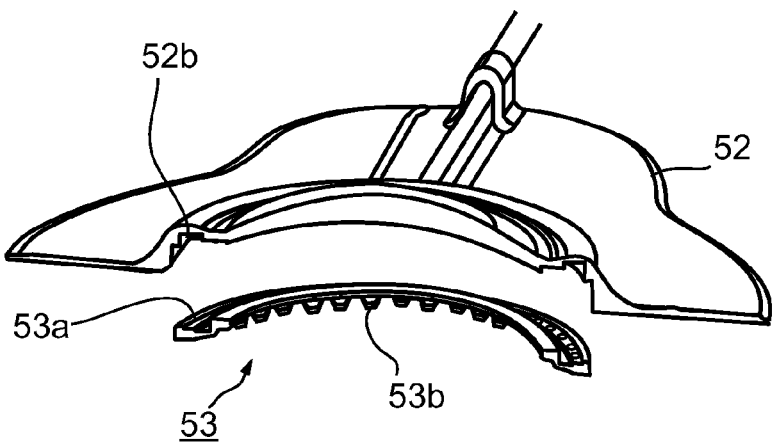
FIGS. 18 and 19 are enlarged fragmentary views from opposite sides more particularly illustrating the structure of the streaming device of FIG. 17.
Figure 19:
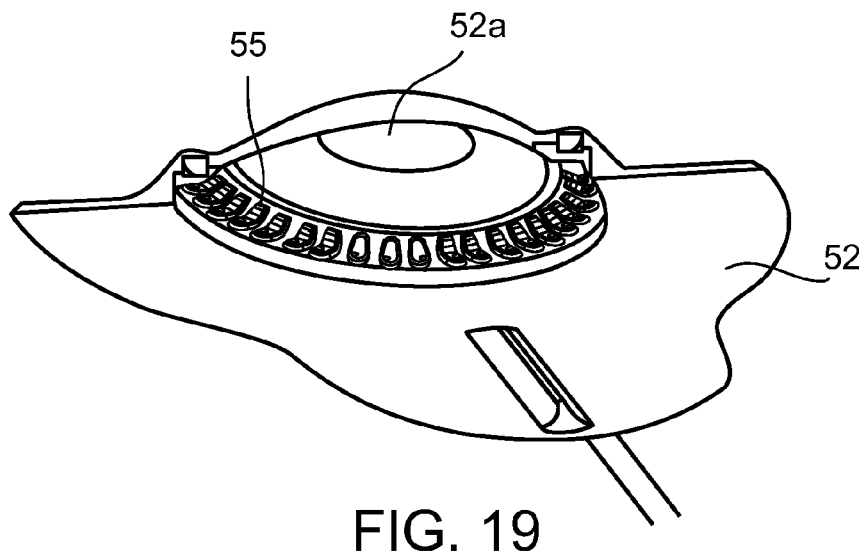

Another construction of streaming device is illustrated in FIGS. 17-19, therein identified as 50, wherein the lower layer 53 is of reduced area as compared to the upper layer 52. Thus, as shown, the lower layer 53 is essentially a partially-circular ring bonded to the under surface of the upper layer 52 and adhesive assembly 54 to define the loop-shaped distribution channel 54 distributing the treating liquid into the treatment chamber enlarged by the dome-shaped, transparent central region 52a.

As shown particularly in FIGS. 18 and 19, layer 53 is formed with a partially-circular recess 53a and with the downwardly-oriented orifices 53b for inletting the treating liquid into the treatment chamber 9 (FIG. 10), and also includes the spacer elements 55, corresponding to spacer elements 23 described above with respect to FIGS. 10-12 for spacing the outlet ends of the orifices from the patient's skin S and the wound W (FIG. 10) so as not to block these orifices when the treatment chamber 9 is subjected to a negative pressure. In addition, the upper layer 52 is also formed with a partially-circular groove 52b to be aligned with groove 53a to define the partially-circular elongated channel feeding the orifices 53b in layer 53. In substantially all other respects, the liquid streaming device illustrated in FIGS. 17-19 is substantially the same as described above and include the adhesive assembly 54 corresponding to adhesive assembly 10 or 10' in FIG. 3a or 3b, respectively.

It will be appreciated that the construction illustrated in FIGS. 17-19 provides basically the same advantages as the construction illustrated in FIGS. 14-16, namely an increase in the flexibility of the streaming device, and a reduction in cost of manufacture because of the significantly smaller amount of elastomeric material used in its production.

FIGS. 20-25 illustrate a still further variation in the construction of the streaming device, therein generally designated 60, in accordance with the present invention. In this variation, both layers 2 and 3 are formed as an integral body 62 of elastomeric material. Body 62 is produced by an injection-molding or casting procedure to form the central recess in the under surface defining the treatment chamber (9, FIG. 10), and the distribution channels (4, 4a) for feeding the treating liquid into and out of the treatment chamber. The latter recess and distribution channels may be formed by including an insert 63 within the mold, which insert is removable after the elastomeric material has been molded as described above in order to define the elongated distribution channel.

The elastomeric material for use in injection-molding or casting the body 62 may be silicone, TPE, or any other suitable elastomeric material. The device 60 illustrated in FIGS. 20-22 also includes a separate adhesive assembly, generally designated 70, which may be of either of the constructions for adhesive assembly 10 described above with respect to FIGS. 3a and 3b. Streaming device 60 may further include the spacer elements shown at 64, described with above with respect to FIGS. 10-12, for spacing the outlet ends of the short distribution ducts or orifices from the patient's skin and wound, as shown particularly in FIGS. 21 and 22.

Figure 20:
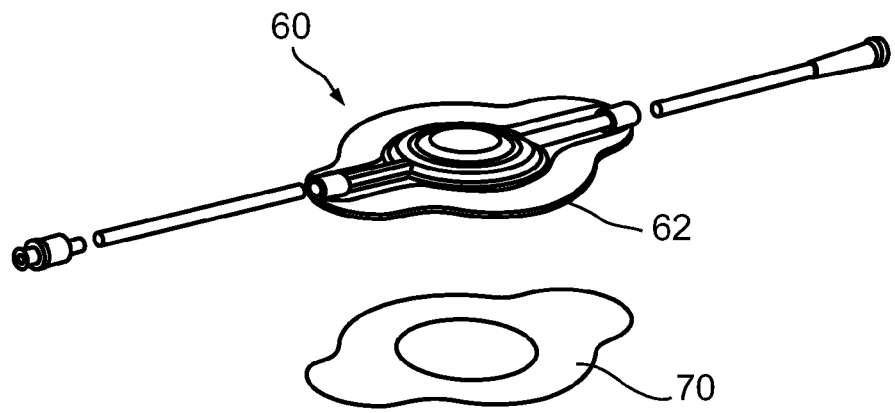
FIG. 20 is an exploded view illustrating a further streaming device constructed in accordance with the present invention, wherein the base is formed as an integral unit by injection molding.
Figure 21:
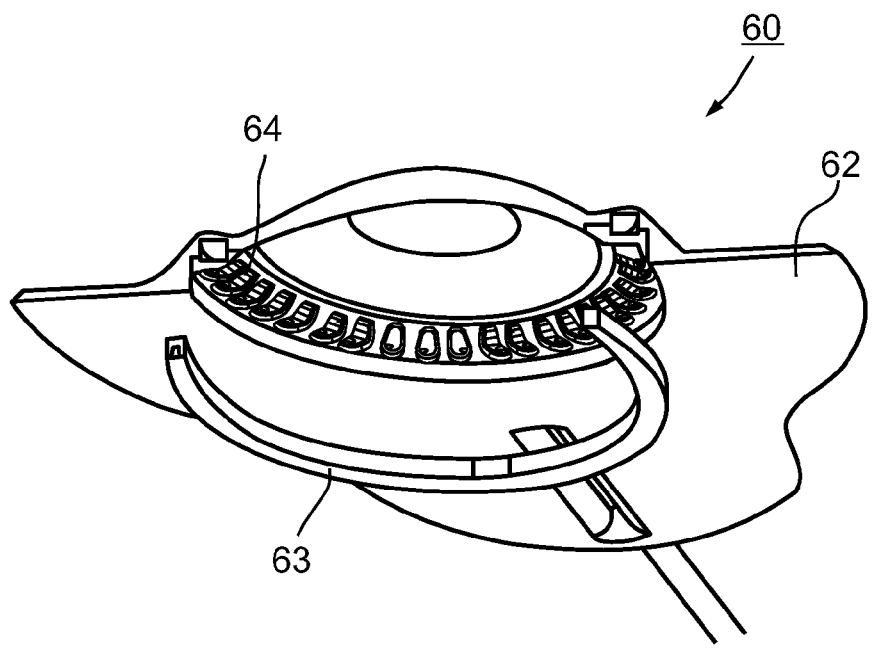
FIGS. 21 and 22 are enlarged fragmentary views more particularly illustrating the manner of injection molding or casting the base of the embodiment of FIG. 20.
Figure 22:
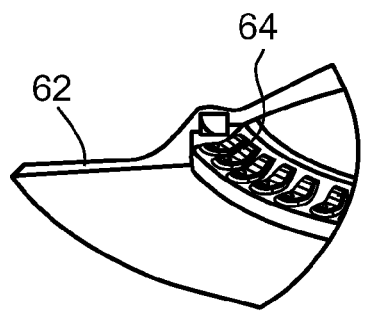
Figure 23:
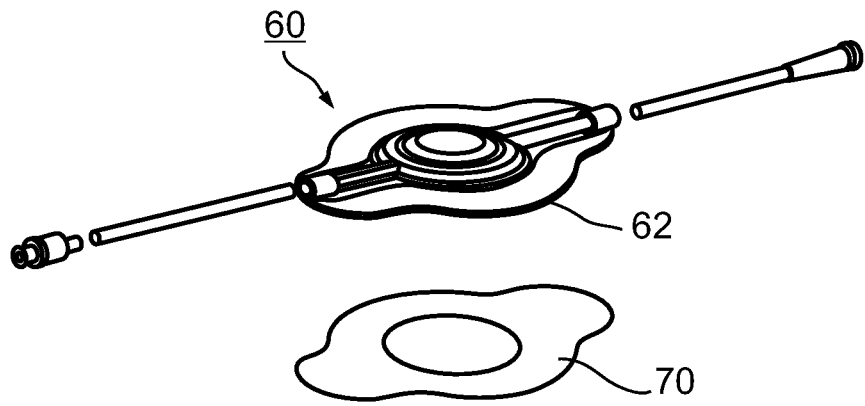
FIGS. 23 and 24 illustrate the streaming device constructed in accordance with the present invention wherein the base is injection molded onto a plastic elastomeric film carrying an adhesive and a release liner.
Figure 24:
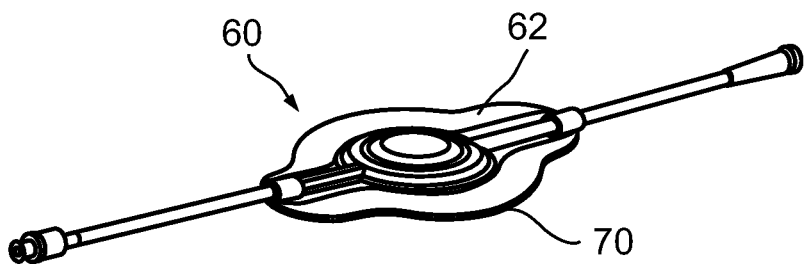
Figure 25:
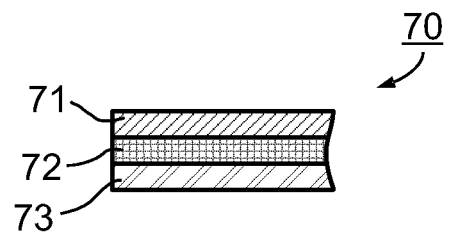
FIG. 25 more particularly illustrates the construction of the plastic film including the adhesive and release liner thereon.

FIGS. 23-25 illustrate a modified construction similar to that of FIGS. 20-22, except here the body 62 is injection molded directly onto the adhesive assembly 70 shown in FIG. 24. In such case, the adhesive assembly 70 could be of the three-layer type illustrated in FIG. 25. It does not require either the upper release liner 14 (FIGS. 3a, 3b) or the upper adhesive layer (e.g., 12, FIG. 3a or 17, FIG. 3b), since the body 62 is injection-molded or cast directly onto the plastic carrier 71, corresponding to carrier 11 in FIG. 3a. Accordingly, as shown in FIG. 25, the adhesive assembly need include only the plastic elastomeric (e.g. silicone) carrier 71 bonded to the injection-molded body 62 during the injection process, the adhesive layer having good adherent properties to the skin, and the release liner 73 for protecting the adhesive layer 72 until ready for application to the subject's skin.

Figure 26:
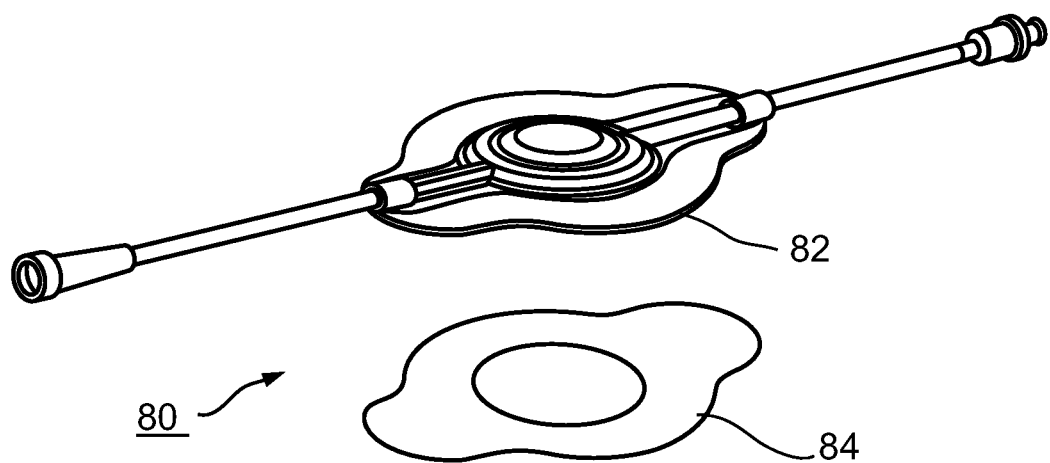
FIG. 26 is an exploded view.
Figure 27:
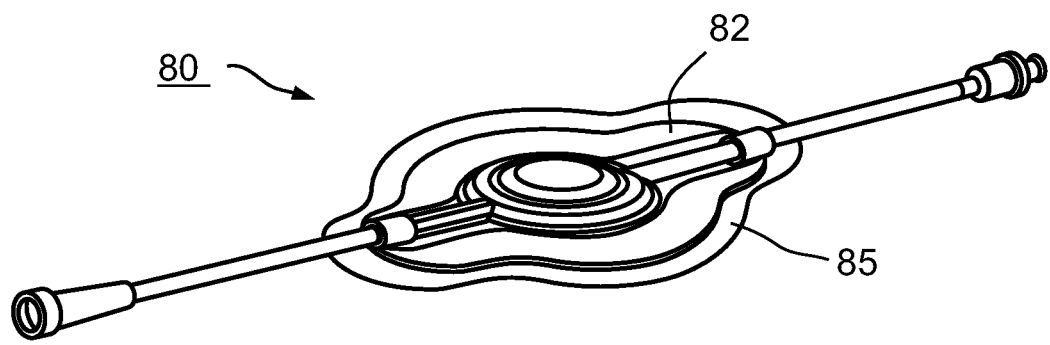
FIG. 27 is an assembled view, illustrating another streaming device constructed in accordance with the present invention in which the adhesive layer is extended to enhance adherence to the patient's skin and sealing of the treatment chamber.

FIGS. 26 and 27 illustrate a further variation, generally designated 80, also including a body, generally designated 82, and an adhesive assembly 84, wherein the adhesive assembly 84 is of larger dimensions than the body 82 so as to produce a marginal extension, shown at 85 in FIG. 27, of the adhesive assembly around the periphery of the body 82 to enhance the adhesion of the streaming device to the skin, and also to enhance its sealing of the treatment chamber.

Figure 28A:
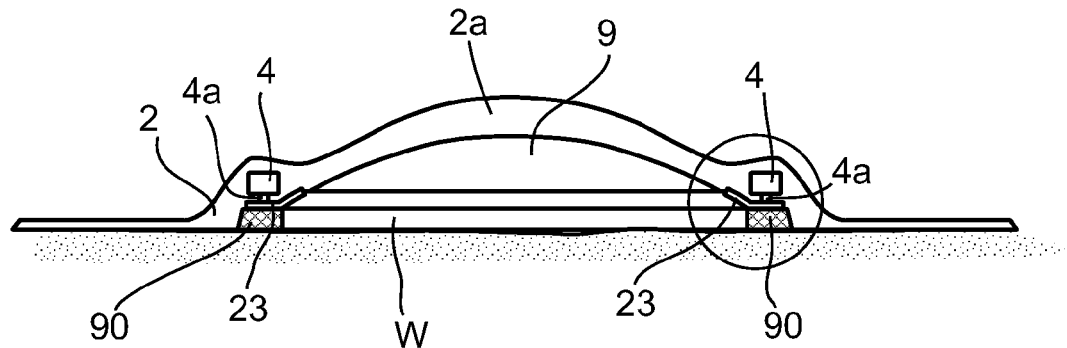
FIGS. 28a-28d illustrate a further feature that may be included in any of the described preferred embodiments for spacing the outlet ends of the distribution ducts from the skin to prevent occlusion of the distribution ducts in the presence of a negative pressure within the treatment chamber.
Figure 28B:
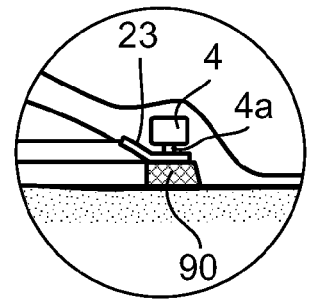
Figure 28C:
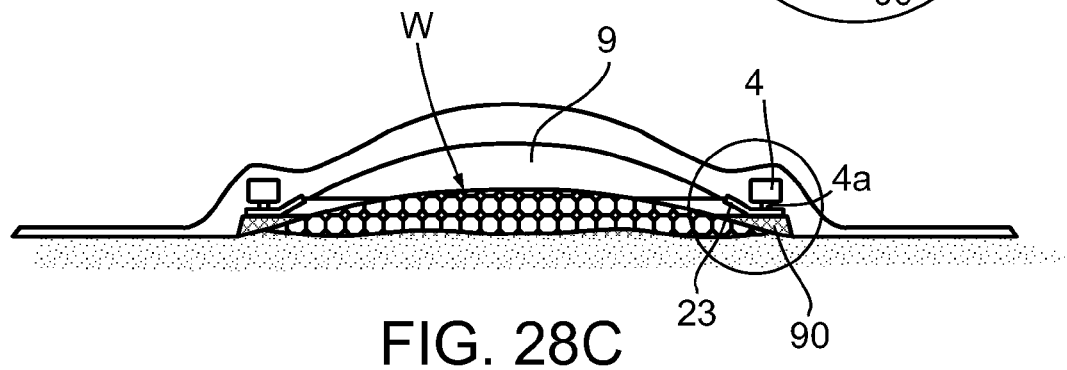
Figure 28D:
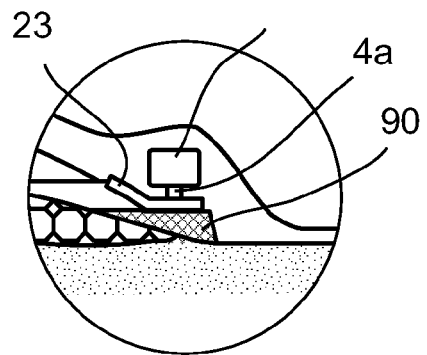

FIGS. 28a-28d illustrate another arrangement for preventing occlusion of the outlets of the short distribution channels in the presence of a high negative pressure within the treatment chamber 9. Thus, whereas FIGS. 10-12 illustrate the provision of spacer elements 23 distributed around the elongated distribution channel 4 for spacing the outlets of the short distribution channels 4a from the skin, FIGS. 28a-28d illustrate the use of a foam ring, therein designated 90, together with the spacer elements 23, for performing this function. Thus, FIGS. 28a and 28b illustrate the condition wherein the treatment chamber 9 is not subjected to a high negative pressure, and FIGS. 28c and 28d illustrate the condition wherein the treatment chamber 9 is subject to a high negative pressure.

In all other respects, the construction illustrated in FIGS. 28a-28d is the same as, and operates in the same manner as, the construction described above with respect to FIGS. 10-12, and therefore corresponding parts have been identified with the same reference numerals.

FIGS. 29-31b illustrate a construction wherein the streaming device, therein generally designated 100, includes a skin guard 102 to protect the patient's skin from solution streaming in the streaming device and also from irritation when the streaming device is removed. Such a skin guard is particularly useful when used with rough skin around the wound, or where the topography around the wound of the streaming device is hard to attach to the patient's skin.

Figure 30:
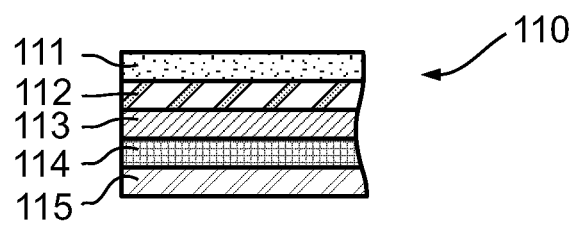
Figure 31A:
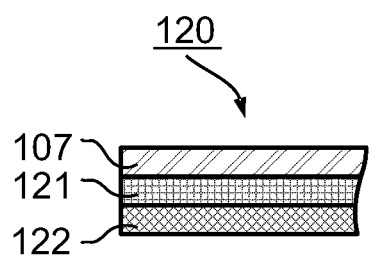
Figure 31B:
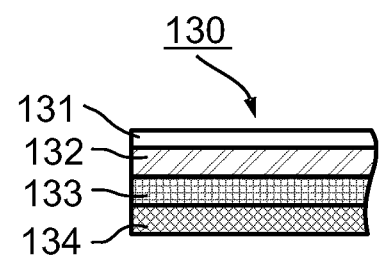

In this construction, the skin guard 102 includes, on its under surface, an adhesive assembly, generally designated 110, of five layers as illustrated in FIG. 30; alternatively, the skin guard 102 may include an adhesive assembly, generally designated 120 in FIG. 31a, or 130 in FIG. 31b.

Figure 29:
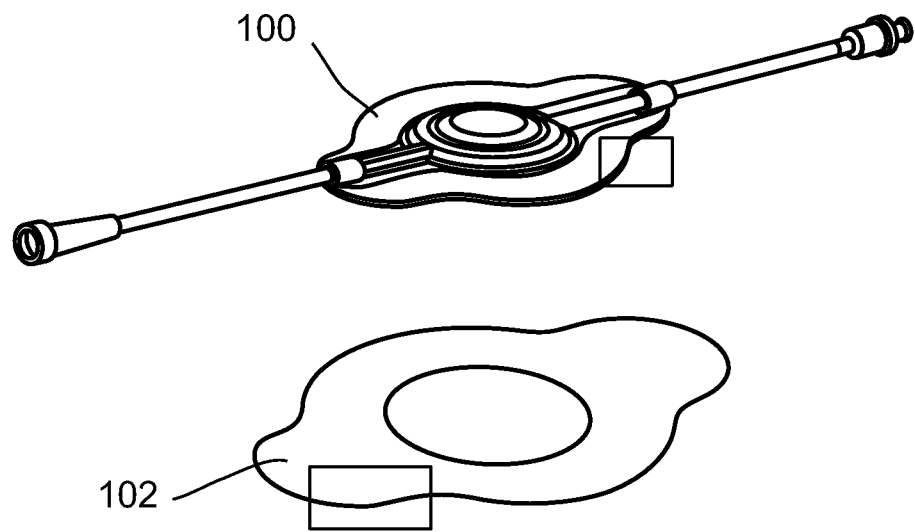
FIGS. 29, 30 and 31a and 31b illustrate the provision of a skin guard between the streaming device and the patient's skin to protect the patient's skin particularly when the streaming device is to be frequently removed and reapplied.

The streaming device 100 illustrated in FIG. 29 is shown as being of a type wherein the body is injection-molded or cast directly onto the skin guard 102. Thus, as shown in FIG. 30, adhesive assembly 110 underlying skin guard 102 includes: injected part 111 of an elastomeric material, such as silicone, TPE, or the like; a release liner 112; a carrier 113 of polyurethane, polyethylene, silicone, TPE, non-woven nylon, or a foamed plastic; an adhesive 114 of an acrylic resin, silicone, rubber, etc.; and a release liner 115.

The skin guard 102 may be of the construction shown at 120 in FIG. 31a, or at 130 in FIG. 31b.

Thus, as shown in FIG. 31a, skin guard 120 may include a layer 107 made of polyurethane, polyethylene, TPE, non-woven fabric such as nylon, or a foamed plastic. Underlying skin guard 107 is a layer of a skin adhesive 121, such as a hydrocolloid, acrylic resin, or rubber. The adhesive layer is protected by a release liner 122, which is peeled away when the skin guard is to be attached to the patient's skin.

FIG. 31b illustrates another construction of the skin guard, wherein the adhesive assembly 130 is separately produced. In this construction, adhesive assembly 130 includes a release layer 131, carrier 132 of polyurethane, polyethylene, TPE, non-woven fabric, or a foamed plastic, as described above. Under the carrier layer 131 is a layer 133 of a skin adhesive, such as a hydrocolloid, acrylic resin, rubber, or the like. Finally, a release liner 134 is applied over the adhesive layer. When using the adhesive assembly 130 illustrated in FIG. 31b, release layer 131 is removed to attach the adhesive assembly to the skin guard, and whenever the skin guard is to be applied to the subject's skin, the lower release liner 134 is removed.

Figure 32:
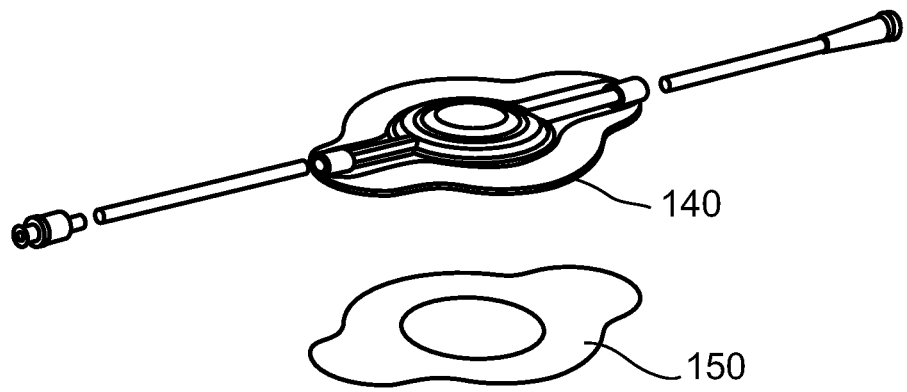
FIG. 32 is an exploded view illustrating a further embodiment wherein the streaming device is molded onto the adhesive assembly.
Figure 33:
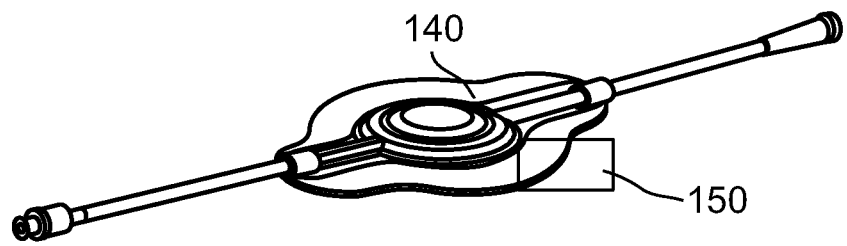
FIG. 33 illustrates the assembled streaming device of FIG. 32.
Figure 34:
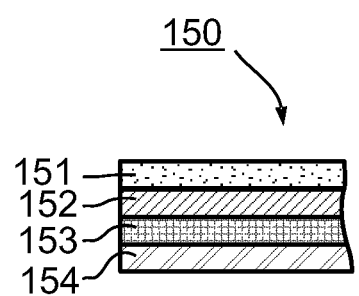
FIG. 34 is a fragmentary view illustrating the construction of the adhesive assembly of FIGS. 32 and 33.
Figure 35:
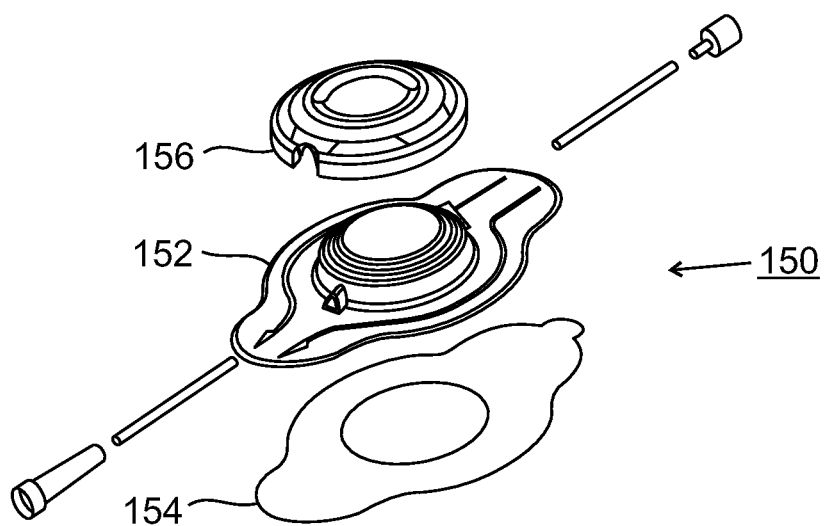
FIG. 35 illustrates another construction wherein the streaming device is closed by a reinforcement cap to ensure structural integrity and to resist manifold collapse due to the negative pressure produced within the streaming device.

FIGS. 32-34 illustrate a further construction similar to that of FIGS. 23-25, wherein the body of the streaming device 140 is injection-molded or cast directly onto the adhesive assembly 150. As shown in FIG. 34, the adhesive assembly 150 in this case includes silicone part 151, injected on carrier 152 of polyurethane, polyethylene, TPE, non-woven fabric, or foamed plastic as described above. The adhesive assembly further includes a skin adhesive layer 153 of a hydrocolloid, an acrylic resin, rubber, or the like; and finally, the adhesive layer 153 is covered by a release liner 154 which is to be removed whenever the streaming device is to be applied to the skin of the patient;

FIG. 35 illustrates a further possible construction of the streaming device, generally designated 150, similar to the construction illustrated in FIGS. 20-25, in which the body 152, serving as the manifold, is formed as an integral body of elastomeric material produced by an injection-molding or casting procedure to include an adhesive layer 154 of any of the previously-described constructions for adhering the body to the skin of the patient. In this case, however, the chamber, within which the wound is located, is closed by a reinforcement cap 156 spaced above the wound to ensure structural integrity and resist collapse of the chamber.

Figure 36:
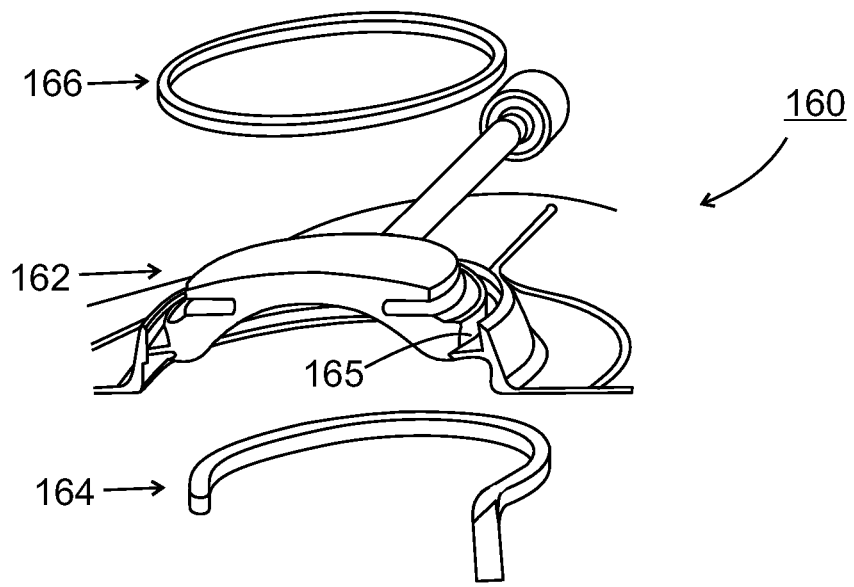
FIG. 36 illustrate a further embodiment of the invention including a separately-formed molded ring applied over the insert for better retaining it in place during the injection molding or casting of the manifold thereover.

FIG. 36 illustrates a still further optional construction of the streaming device to facilitate its production by injection-molding or casting. The streaming device in FIG. 36, generally designated 160, also includes an injection-molded or cast body 162, serving as the streaming manifold, embedding the insert 164 producing elongated distribution channel 165 for distributing the inletted liquid into the treatment chamber enclosing the wound (e.g. W, FIG. 10). In this case, however, the streaming device further includes a pre-molded ring 166 overlying the insert 164 to facilitate fixing the location of the latter insert during the injection-molding or casting of the streaming manifold 162 thereover, as described below with respect to FIGS. 40-41b.

Figure 37:
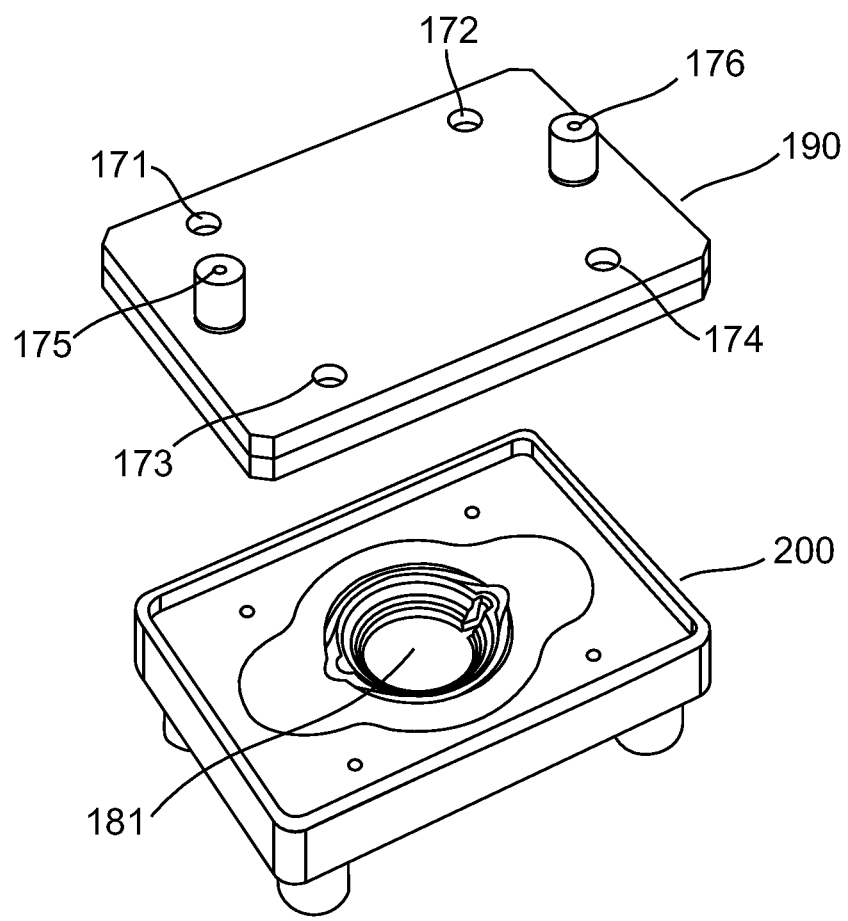
FIGS. 37-39 illustrate top and bottom molds which may be used to produce a streaming device having an adhesive bottom layer exhibiting good adhesion properties on one to the streaming device, and on the opposite side to the subject's skin.
Figure 38:
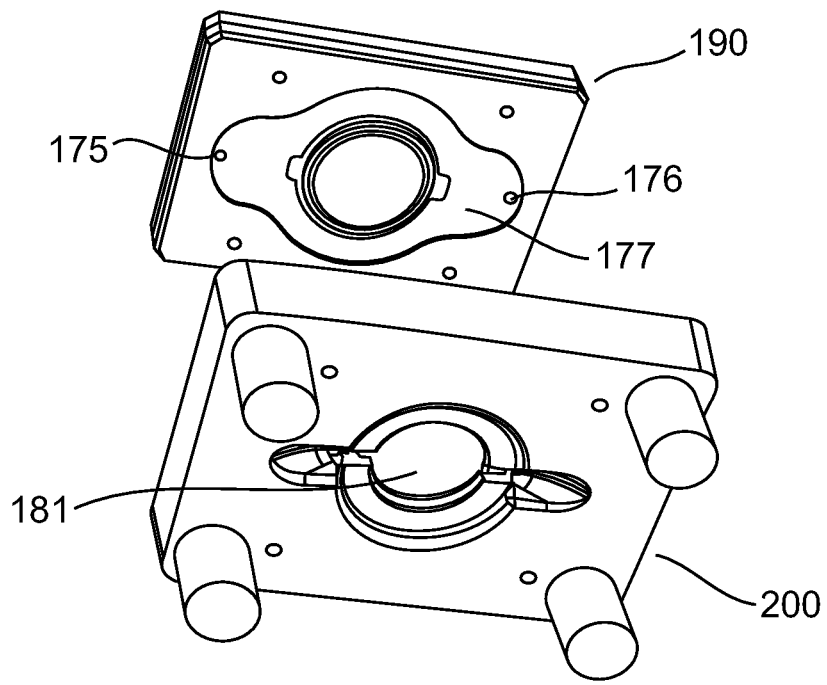
Figure 39:
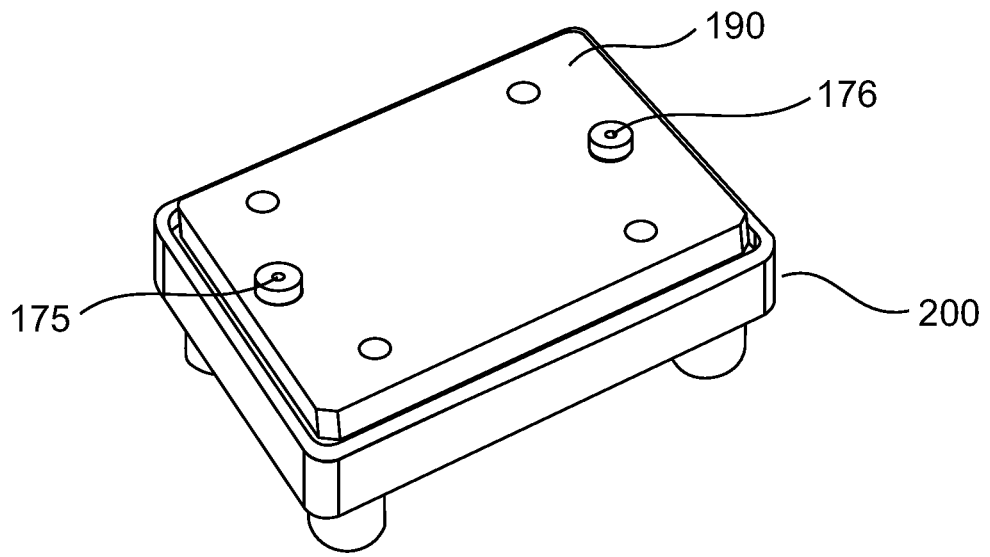

FIGS. 37-39 illustrate a preferred manner of applying a liquid or semi-liquid adhesive to the streaming manifold instead of a laminated adhesive.

Thus, as shown particularly in FIG. 37, the mold for applying the adhesive includes a top mold plate 170 and a bottom mold plate 180. The top mold plate 170 is formed with four threaded holes 171-174 for receiving screws for fastening it to the bottom mold plate 180. In addition, the top mold plate 170 is formed with an inlet 175 for inletting the liquid or semi-liquid adhesive (e.g. a silicone), and an outlet 176 for outletting the excess. In addition, as shown particularly in FIG. 38, the under surface of the top mold plate 170 is formed with a cavity 177 to receive the adhesive. As further seen in FIG. 38, the bottom mold plate 182 is formed with an opening 181 for defining the opening for receiving the streaming device.

The adhesive used could be one selected to have good adherent properties to both the material of the streaming device, as well as to the skin of the subject receiving the streaming device. Two-part adhesives are known that could be used for this purpose.

FIG. 36 illustrates a still further optional construction of the streaming device to facilitate its production by injection-molding or casting. The streaming device in FIG. 36, generally designated 160, also includes an injection-molded or cast body 162, serving as the streaming manifold, embedding the insert 164 producing elongated distribution channel 165 for distributing the inletted liquid into the treatment chamber enclosing the wound (e.g. W, FIG. 10). In this case, however, the streaming device further includes a pre-molded ring 166 overlying the insert 164 to facilitate fixing the location of the latter insert during the injection-molding or casting of the streaming manifold 162 thereover, as described below with respect to FIGS. 40-41b.

FIGS. 37-39 illustrate a preferred manner of applying a liquid or semi-liquid adhesive to the streaming manifold instead of a laminated adhesive.

Thus, as shown particularly in FIG. 37, the mold for applying the adhesive includes a top mold plate 190 and a bottom mold plate 200. The top mold plate 190 is formed with four threaded holes 171-174 for receiving screws for fastening it to the bottom mold plate 200. In addition, the top mold plate 190 is formed with an inlet 175 for inletting the liquid or semi-liquid adhesive (e.g. a silicone), and an outlet 176 for outletting the excess. In addition, as shown particularly in FIG. 38, the under surface of the top mold plate 190 is formed with a cavity 177 to receive the adhesive. As further seen in FIG. 38, the bottom mold plate 200 is formed with an opening 181 for defining the opening for receiving the center of the streaming device.

The adhesive used could be one selected to have good adherent properties to both the material of the streaming device, as well as to the skin of the subject receiving the streaming device. Two-part adhesives are known that could be used for this purpose.

FIG. 39 illustrates the two part molds 190, 200 in a closed condition, ready for injecting the liquid or semi-liquid adhesive.

Figure 40:
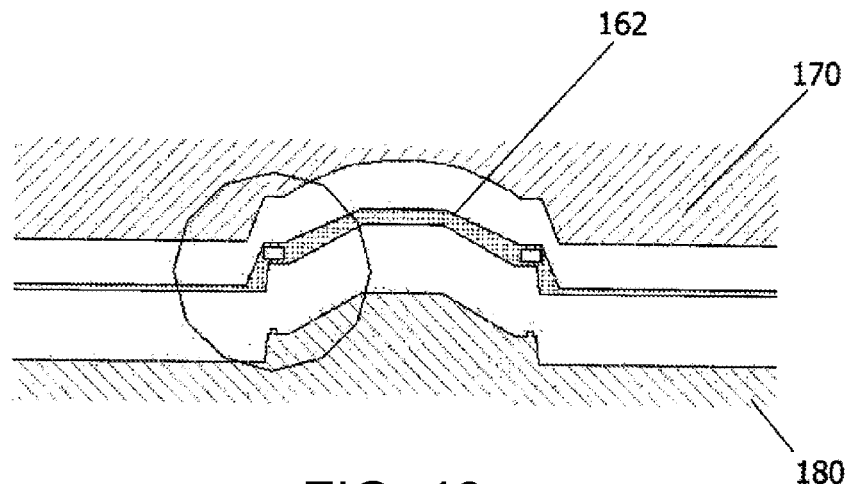
FIGS. 40, 41a and 41b illustrate the structure of the top and bottom molds cooperable with the mold ring for producing the streaming device of FIG. 39.
Figures 41A, 41B:
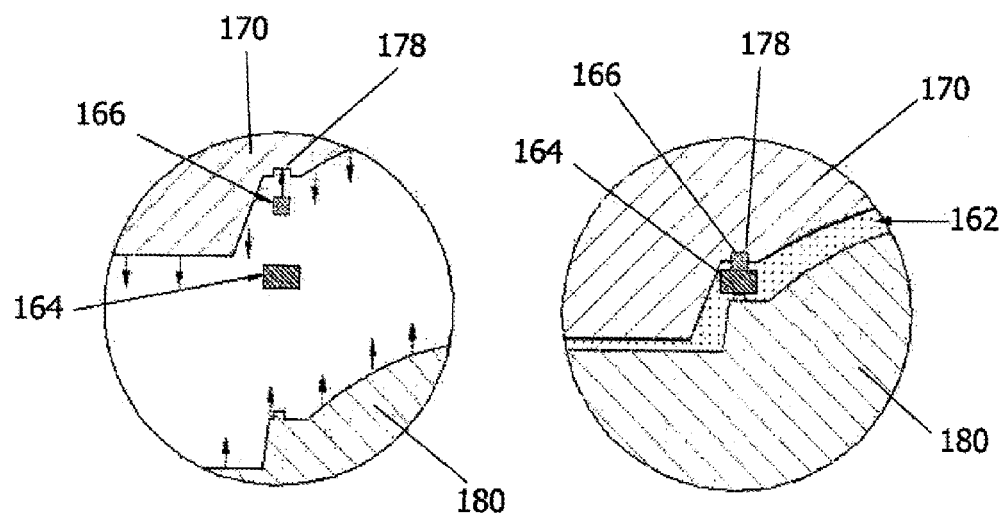

FIG. 40 schematically illustrates the production of the streaming device by injection-molding or casting using the mold plates 170, 180; whereas FIGS. 41a and 41b schematically illustrate the manner in which the pre-molded ring 166 (FIG. 36) applied over the elongated distribution channel insert 164, serves to locate this insert between the two mold plates 170, 180 during the molding operation. Thus, as seen in FIG. 41a, the under surface of the top mold plate 170 is further formed with an annular groove 178 for receiving the pre-molded ring 166 applied over the elongated distribution channel insert 164 to properly locate the latter during the molding or casting operation of the streaming manifold 162 thereover, as shown in FIG. 41b.

While the invention has been described with respect to many preferred embodiments, it will be appreciated that these are set forth merely for purposes of example, and that many other variations, modifications and applications of the invention may be made.

What is claimed is:

1. A liquid streaming device for treating a wound, comprising:
    a body having a lower surface for application to skin region around the wound to be treated and to conform to the contour of the skin region, and an upper surface facing outwardly when the body is applied to the skin region;
    a recess formed in the lower surface of the body and configured to enclose the wound when the body is applied to the skin region, and to define a chamber closed on one side by the skin region and the wound, and on the opposite side by the body;
    an inlet in the body on one side of the recess for introducing a treating liquid into an inlet side of the chamber; and
    an outlet in the body on another side of the recess for outletting the treating liquid from an outlet side of the chamber;
    wherein said one side and said another side are opposing sides; wherein the device further comprises an at least partially circular elongated distribution channel in the body for conducting the treating liquid from the inlet to said chamber via a plurality of orifices;
    wherein the elongated distribution channel in the body extends around the inlet side of the chamber defined by the recess; the elongated distribution channel communicating with a plurality of short distribution channels spaced along the elongated distribution channel for distributing the treating liquid into the inlet side of the chamber defined by the recess.

2. The device according to claim 1, wherein the plurality of short distribution channels have outlets oriented to direct the treating liquid substantially downwardly into the wound.

3. The device according to claim 1, wherein the elongated distribution channel is configured as an open loop having closed ends spaced from each other to define an interruption in the open loop between the closed ends;
    the plurality of short distribution channels being spaced along the loop to communicate with the inlet side of the chamber;
    the interruption in the loop constituting the outlet side of the chamber and communicating with said outlet of the body.

4. The device according to claim 1, wherein the outlets of the short distribution channels are spaced away from the wound to prevent blockage of the outlets when the chamber is under a negative pressure.

5. The device according to claim 4, wherein the outlets of the short distribution channels are spaced away from the wound by a plurality of spacing elements interposed between the outlets of the short distribution channels and the skin of the patient.

6. The device according to claim 4, wherein the outlets of the short distribution channels are spaced away from the wound by a strip of foam material interposed between the outlets of the short distribution channels and the skin of the patient.

7. The device according to claim 1, wherein an outer surface of the body overlying the recess is of dome shape to resist its collapse into contact with the wound by a negative pressure within the chamber.

8. The device according to claim 1, wherein at least the portion of the body overlying the recess is transparent to permit visual observation of the interior of the chamber.

9. The device according to claim 1, wherein the body includes an inlet opening in its upper surface communicating with a central region of the chamber, and an inlet conduit extending through the inlet opening into the chamber for inletting a treating liquid therein to treat deep wounds.

10. The device according to claim 9, wherein the body is of an elastomeric material.

11. The device according to claim 9, wherein the inlet and outlet of the body include tubes having inlet and outlet connectors for connecting them, respectively, to a source of treating liquid and to a collection receptacle for receiving the treating liquid after exiting from the chamber, and wherein said inlet connector is a luer-type connector including a valve which is self-closing when the connector is detached from the source of treating liquid.

12. The device according to claim 1, wherein the body is a thin flexible body of enlarged area at its center region for accommodating the chamber, and is of relatively small area at its opposite end regions for accommodating the inlet and outlet.

13. The device according to claim 1, wherein the body further includes an adhesive layer on its lower surface for adhering the body to a skin region around the wound and for sealing the chamber.

14. The device according to claim 13, wherein said adhesive layer is part of an adhesive assembly of larger dimensions than those of said body so as to produce a marginal extension around the periphery of said body to enhance its adhesion to the skin, and its sealing of said chamber.

15. The device according to claim 1, wherein said streaming device further includes a thin flexible layer to underlie the lower surface of said body, said thin flexible layer being provided with an upper adhesive layer for adhering to said body, and a lower adhesive layer for adhering to the patient, such that said further thin flexible layer serves as a skin guard when adhering the streaming device to the patient.

16. The device according to claim 1, wherein said opposite side of the body closing said chamber is in the form of a reinforcement cap spaced above the wound to ensure structural integrity and to resist collapse of the chamber.

17. The device according to claim 1, wherein said elongated distribution channel is embedded in a body of injection-molded elastomeric material; said device further comprising a liquid or semi-liquid adhesive having good adherent properties both to the body and the skin region.

18. A liquid streaming device for treating a wound, comprising:
a body having a lower surface for application to skin region around the wound to be treated and to conform to the contour of the skin region, and an upper surface facing outwardly when the body is applied to the skin region;
a recess formed in the lower surface of the body and configured to enclose the wound when the body is applied to the skin region, and to define a chamber closed on one side by the skin region and the wound, and on the opposite side by the body;
an inlet in the body on one side of the recess for introducing a treating liquid into an inlet side of the chamber; and
an outlet in the body on another side of the recess for outletting the treating liquid from an outlet side of the chamber;
wherein said one side and said another side are opposing sides;
wherein the device further comprises an at least partially circular elongated distribution channel in the body for conducting the treating liquid from the inlet to said chamber via a plurality of orifices;
wherein said device further comprises a pre-molded ring overlying a removable insert defining, when removed, said elongated distribution channel and embedded therewith in said body of injection-molded elastomeric material for fixing the location of the elongated distribution channel within said body of injection-molded elastomeric material.

* * * * *